United States Patent [19]

Flach et al.

[11] Patent Number: 5,205,294

[45] Date of Patent: Apr. 27, 1993

[54] APPARATUS AND METHODOLOGY FOR DIGITAL TELEMETRY OF BIOMEDICAL SIGNALS

[75] Inventors: Terry E. Flach, Altadena; William C. McBride, Corona Del Mar, both of Calif.

[73] Assignee: Pacific Communications, Inc., Santa Ana, Calif.

[21] Appl. No.: 656,704

[22] Filed: Feb. 19, 1991

[51] Int. Cl.$^5$ ............................................. A61B 5/0402
[52] U.S. Cl. ...................................... 128/696; 128/903
[58] Field of Search ................................. 128/903, 696

[56] References Cited

U.S. PATENT DOCUMENTS

| | | | |
|---|---|---|---|
| 3,953,848 | 4/1976 | Dillman et al. | 128/903 |
| 3,972,320 | 8/1976 | Kalman | 128/903 |
| 4,958,645 | 9/1990 | Cadell et al. | 128/903 |

Primary Examiner—William E. Kamm
Assistant Examiner—Scott M. Getzow
Attorney, Agent, or Firm—Daniel L. Dawes

[57] ABSTRACT

Biomedical information is directly digitally telemetered from the patient through a frequency modulated transmitter to a remote receiver and computer station. DC offset on the biopotential leads and signals from the patient is compensated by converting the output of the amplifier, such as an electrocardiographic amplifier, into digital format, determining the average or DC component of the digital signal, and generating a digital correction word which is then converted into analog form and fed back into the input of the electrocardiographic amplifier to cancel out the DC offset. The same circuitry is used to insert a standard test signal instead of a correction signal and the output of the amplifier is then checked not to determine its DC component, but to determine whether or not the gain of the electrocardiographic amplifier is performing at a predetermined calibration point. If not, a digital correction word is generated and provided as a correction signal to the programmable gain amplifier.

11 Claims, 5 Drawing Sheets

APPARATUS AND METHODOLOGY FOR DIGITAL TELEMETRY OF BIOMEDICAL SIGNALS

BACKGROUND OF THE INVENTION

1. Field of the Invention

The invention relates to the field of telemetry used in biomedical applications and in particular to telemetry of digital biomedical data, including in particular digital telemetry of cardiac signals.

2. Description of the Prior Art

Telemetry systems that transmit a plurality of patient biosignals, such as ECG signals, are well known. A number of patients, such as may be cared for in an intensive care unit will each be coupled to a transmitter at the patient's location. The telemetry unit transmits to a central nurses' station, which monitors a plurality of patient transmitters through a multiplexing arrangement. Any biomedical signal may be telemetered, but cardiac signals or ECG signals, blood pressure, respiration rates, pulse rates and other vital signs are typically monitored through conventional means and transmitted to the nurses' monitoring station. Personnel may thereby continuously monitor the vital signs of a large number of patients. In addition, one or more of the vital signs for each of the patients may be coupled to a software driven alarm in the event that an abnormality is detected.

The analog data which is transmitted is often susceptible to large DC biases picked up by the ECG leads of other biomedical instrumentation leads and transmitted as true data. In addition, depending on the bit patterns, prior digital data would have intervals of high ones density or high zeroes density which in frequency modulated data tend to cause a average droop or tilt transmitted as a DC drift.

This DC drift not only plays havoc with alarm settings in the monitoring station, but also requires additional dynamic range or bandwidth and hence has effect of reducing the sensitivity of the receiving circuitry at the monitoring station. In addition, frequency modulated analog data typically has to be converted to digital data for more sophisticated and varied processing in the monitoring station, for example, for the recognition of a particular type of cardiographic pattern, which may be indicative of a heart behavior more subtle than cardiac arrest.

Therefore, what is needed is an apparatus and methodology for telemetering the biomedical data in digital form in a manner such that the biases introduced through the ECG leads and other medical probes do not corrupt the data or require complex electronic or software compensations.

BRIEF SUMMARY OF THE INVENTION

The invention is an improvement in a biomedical apparatus for monitoring biopotentials derived from a patient comprising an instrumentation circuit for detecting the biopotentials from the patient and for providing an analog signal at the patient corresponding thereto. An analog-to-digital conversion circuit converts the analog signals corresponding to the biopotential signals to digital format at the situs of the patient. A transmitter circuit telemeters digital signals corresponding to the digitized biopotential signals generated by the analog-to-digital conversion circuit. As a result, biomedical information is directly telemetered from a patient in digital format.

The improvement further comprises a receiver circuit for receiving the telemetered digital signal, and a computer circuit coupled to the receiver circuit for processing the digital signals received by the receiver circuit at a central station remote from the patient.

The transmitter circuit uses a phase-locked loop to generate the output transmitter frequency. A voltage controlled oscillator generates the output frequency. A crystal stabilized voltage controlled oscillator (VCXO) provides a reference frequency for the output voltage controlled oscillator. A digital frequency counter, phase detector, and loop filter comprise the remaining components of the phase-locked loop. By modulating the reference voltage controlled crystal oscillator with a signal related to the average value of the digital bit pattern, and the output voltage controlled oscillator with the total digital signal the circuit may compensate for the DC or low frequency content of the data pattern.

The transmitter circuit is a tunable frequency modulated radio transmitter. The digital signals have a pattern. The tunable frequency modulated radio transmitter comprises an averaging circuit for averaging the pattern of the digital signals to generate a DC value signal of the pattern. A first voltage controlled crystal oscillator circuit has its control input coupled to the averaging circuit. The first voltage controlled crystal oscillator circuit generates a variable reference frequency dependent upon the DC value signal of the pattern of the digital signals. A phase detector has its input coupled to the output of the first voltage controlled crystal oscillator circuit. A loop filter has an input coupled to an output of the phase detector. A second voltage controlled oscillator circuit has its control input coupled to an output of the loop filter. The output of the second voltage control oscillator oscillates at an output frequency within the desired band of the modulated radio transmitter. A divider circuit feeds back the output frequency to the phase detector divided by a predetermined integer. The AC components of the digital data is also coupled into the input of the second voltage controlled oscillator circuit so that the output frequency of the second voltage controlled oscillator circuit is frequency modulated by the digital data. DC offset, caused by data bias, is compensated by the DC value signal corresponding to an average DC value of the bit pattern of the digital data.

The phase-lock-loop circuit in one embodiment also comprises a microcontroller coupled to a lock detect signal from the phase detector. The lock detect signal signifies whether or not the phase-lock-loop circuit has achieved lockup and if not, whether the desired frequency is greater or less than that at which the voltage controlled oscillator is positioned. A digital-to-analog converter is coupled to the microcontroller and controlled thereby. The digital-to-analog converter has an output coupled in turn to the voltage controlled oscillator to preposition the voltage controlled oscillator at a frequency as determined by input to the digital-to-analog computer from the microcontroller.

In one embodiment the voltage controlled oscillator comprises a first varicap diode circuit controlled by the output of the loop filter for fine tuning the voltage controlled oscillator. A second varicap diode circuit is controlled by the output from the digital-to-analog converter for prepositioning the voltage controlled oscillator at a predetermined frequency.

The improvement further comprises an analog-to-digital converter having an input coupled to the output of the loop filter and an output coupled to the microcontroller. The microcontroller monitors the output of the analog-to-digital converter and generates an error compensation signal which is coupled to the digital-to-analog converter in order to maintain the voltage controlled oscillator at a predetermined operating point notwithstanding component drift caused by large temperature shifts.

The voltage controlled oscillator has a tuning curve relating frequency of operation and tuning voltage input in the voltage controlled oscillator. The tuning curve is nonlinear. The microcontroller further comprises a memory circuit for storing the tuning curve. The microcontroller provides a control signal to the digital-to-analog converter for prepositioning the frequency of the voltage controlled oscillator so that the closed loop bandwidth of the phase-locked loop remains substantially constant even in the event of large variations in the control divider's divide ratio.

The instrumentation circuit comprises a biopotential amplifier. The biopotential amplifier receives the biopotential signals from the patient and generates an output signal. The improvement further comprises a microcontroller having an input coupled to the output signal. A digital-to-analog converter has an input coupled to the microcontroller. An output of the digital-to-analog converter is fed back to the amplifier as a correction signal. The microcontroller determines what the DC value of the output signal is and generates a correction signal which is coupled to the input of the digital-to-analog converter so that the DC value is removed from the output signal by signal compensation into the input of the amplifier.

The improvement further comprises another digital-to-analog converter having an input coupled to the microcontroller and an output coupled to the amplifier. The amplifier is a programmable gain amplifier with adjustable gain controlled by the other digital-to-analog converter. The microcontroller is programmed to selectively provide a standardized test signal which is fed back through the digital-to-analog converter to the amplifier. The microcontroller measures the output signal from the amplifier and generates a control signal through the other digital-to-analog converter to adjust the gain of the amplifier so that the gain is calibrated to a predetermined value.

The invention is also a method for compensating data bias in the digital information provided to a phase-lock-loop circuit comprising the steps of averaging a digital signal to obtain a DC value representative thereof. A first reference frequency is generated according to the DC value. More specifically, the method compensates the effects of data bias in digital NRZ signals used to modulate the voltage controlled oscillator in phase-locked loop frequency sources. The reference frequency is changed in a direction to counteract the DC value of the data bias. A control voltage is generated from the first reference frequency by means of a phase detector and loop filter. An output frequency is generated from a voltage controlled oscillator in response in part to the generated control voltage. The output frequency is divided by a divider. The divided output frequency is fed back to the phase detector to provide a phase-lock loop through the phase detector, loop filter, voltage controlled oscillator and divider. The output frequency is frequency modulated by the digital signals by providing the digital signals to the input of the voltage controlled oscillator.

The invention is still further an improvement in a method of prepositioning the frequency within a voltage controller oscillator of a phase-lock-loop circuit comprising a phase detector coupled with a loop filter. The loop filter is coupled to the voltage controlled oscillator and a divider couples the output of the voltage controlled oscillator back to the phase detector to provide the phase locked loop. The improvement comprising the steps of determining whether the voltage controlled oscillator is locked and, if not, in what direction a control voltage provided to the voltage controlled oscillator ought to be driven. A control word is generated in a microcontroller and the control word converted into an analog signal which is coupled to the voltage controlled oscillator to position the voltage controlled oscillator at a preselected frequency within the voltage controlled oscillator's frequency range. The voltage controlled oscillator is prepositioned by the generated analog signal, corresponding to the word, to a frequency as determined by the microcontroller.

The step of prepositioning the voltage controlled oscillator is performed within a first frequency determining circuit in the voltage controlled oscillator, which first sets the operating frequency within the oscillator within the bandwidth, and within a second frequency determining circuit in the voltage controlled oscillator, which second circuit is utilized within the phase-lock-loop circuit for fine tuning the voltage controlled oscillator.

The invention is also a method for DC offsetting an output from an amplifier comprising the steps of converting the output signal to a digital signal. The digital signal is coupled to a microcontroller. A correction word is generated in the microcontroller proportional to the DC content in the output signal as determined by the microcontroller. The DC offset of the output signal is calculated within the microcontroller. The digital word from the microcontroller is converted into an analog DC correction signal. The DC correction signal is coupled to an input of the amplifier to compensate for the DC offset within the output signal.

The invention is further a method of calibrating an analog amplifier comprising the steps of generating a standard digital test word in a microcontroller upon each power up. The standard test word is converted into an analog signal. The analog signal is coupled to an input of the analog amplifier. The test signal is amplified by the analog amplifier to produce an analog output signal. The analog output signal is converted into a digital output signal. The digital output signal corresponding to the output signal is coupled to the microcontroller. It is then determined from the digital output signal whether the analog amplifier has a predetermined calibrated gain. A word is generated within the microcontroller to correct the gain of the amplifier as determined by the microcontroller. The correction word is used to set the gain of a gain programmable amplifier.

The invention is better visualized by now turning to the following drawings wherein like elements are referenced by like numerals.

BRIEF DESCRIPTION OF THE DRAWINGS

FIG. 8 is a flow diagram of the methodology practiced in connection with the circuit of FIG. 7a.

FIG. 9 is a graph of the tuning curve of a voltage controlled oscillator such as shown in FIG. 7a.

The various embodiments in the invention may be understood by now turning to the following detailed description.

DETAILED DESCRIPTION OF THE PREFERRED EMBODIMENTS

Biomedical information is directly digitally telemetered from the patient through a frequency modulated transmitter to a remote receiver and computer station. DC offset on the biopotential leads and signals from the patient is compensated by converting the output of the amplifier, such as an ECG amplifier, into digital format, determining the average or DC component of the digital signal, and generating a digital correction word which is then converted into analog form and fed back into the input of the ECG amplifier to cancel out the DC offset.

The same circuitry is used to insert a standard test signal instead of a correction signal and the output of the amplifier is then checked not to determine its DC component, but to determine whether or not the gain of the ECG amplifier is performing at a predetermined calibration point. If not, a digital correction word is generated, and connected to a digitally controlled programmable gain amplifier.

The phase-lock-loop circuit in the digital transmitter compensates for data bias by averaging and generating a scaled measure of the DC content of the digital data fed into the phase-lock-loop circuit. The average value of the digital data provides a small correction signal to a voltage controlled reference oscillator. In this embodiment the oscillator uses a voltage controlled oscillator which provides the reference frequency input for the phase-locked loop. The digital data modulates the reference voltage controlled oscillator by directly coupling the digital signal to the frequency control input of the reference voltage controlled crystal oscillator.

Further control of the phase-lock-loop circuit in the transmitter is achieved by pretuning the operating frequency of the output voltage controlled oscillator by means of a microcontroller. The input to the microcontroller is a data word corresponding to the operating frequency. The microcontroller is then used to implement an algorithm is set the operating frequency of the output voltage controlled oscillator at a preselected point within the operating range in the phase-lock-loop circuit. The operating point of the phase-lock-loop circuit is set by a first varicap diode while fine tuning of the voltage controlled oscillator is provided by a second varicap diode. The operating point of the voltage controlled oscillator is set in such a position of the tuning curve of the voltage controlled oscillator that the tuning gain of the oscillator approximately compensates for any changes in the dividing integer used in the divider in the phase-lock-loop circuit.

Figure 1:
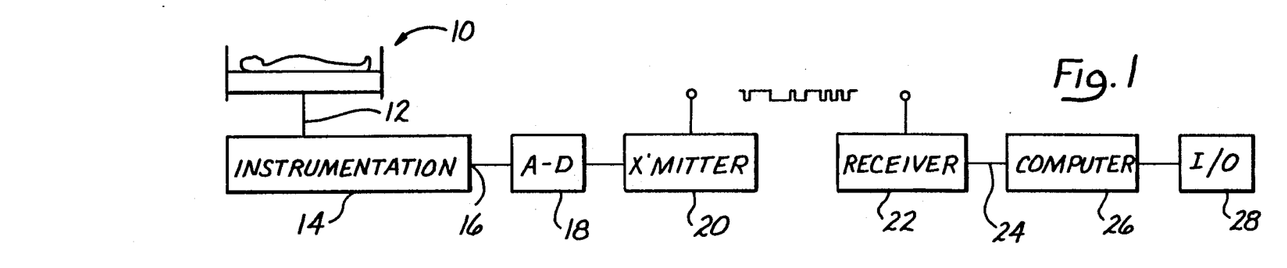
FIG. 1 is a block diagram of the application wherein the invention is employed, namely in the digital telemetry of patient monitoring.

FIG. 1 is a block diagram of the application of the invention wherein a patient 10 is coupled to a plurality of biomedical instrumentation leads 12. Leads 12 are then coupled to conventional biomedical instrumentation 14. For example, in the illustrated embodiment leads 12 comprise a plurality of ECG leads coupled into ECG amplifiers as part of the instrumentation 14. Many other types of signals and leads could also be coupled between patient 10 and instrumentation 14 by leads 12. ECG signals will be described as the illustrated embodiment only because ECG signals are generally the most complex signals which are typical monitored.

A plurality of analog signals corresponding to the plurality of biomedical signals sensed from patient 10 are provided at output 16 of instrumentation 14. The analog signals are then converted into digital form by a conventional A-to-D converter 18 and transmitted as FM modulated digital data by transmitter 20 by means described in more detail below. In the illustrated embodiment transmissions are low power FM transmissions made in the 174-216 Mhz band. Signals strengths at 30 meters of approximately 100 microvolts per meter are typical. Transmitter 20 may transmit on any one of a plurality of channels, spaced approximately 100 kHz apart. It is to be clearly understood that other frequencies and bandwidths may be used in connection with the invention without departing from its scope and spirit.

The FM signal is received by an FM receiver 22 which is a fully frequency synthesized receiver. The digital signals are demodulated by receiver 22, buffered, conditioned and provided as conventional serial digital data on output 24 to a conventional computer 26 which includes memory. Computer 26 also has a plurality of conventional input and output devices 28 such as a plurality of monitors, keyboards, modems, plotters, mass storage devices and the like.

As described below, transmitter 20 includes a tunable modulated radio transmitter to send cardiac or other biomedical information directly from the patient's situs. The tunable phase-lock-loop circuit used in the transmitter has an approximate 6 Mhz tuning range and is a frequency shift keyed (FSK) transmitter using a non-return zero (NRZ) data format. As illustrated below, the invention reduces the occupied bandwidth of the modulated transmitter output by as much as a factor of two and obviates the requirement for any threshold tracking circuits in the FSK receiver 22.

Further according to the invention, instrumentation 14 includes a microcontroller DC tracking loop used for DC offset compensation in the ECG amplifiers. This allows the ECG amplifiers to exhibit a frequency response extending to DC for finite periods of time, and allows for software selectable recovery times from the DC offset signal.

Further, the microcontroller DC tracking loop in the ECG amplifiers allows for recalibration of the voltage amplification of each ECG amplifier to a nominal center value upon each power-up of instrumentation 14. This obviates the need for manual calibration and alignment of the amplifiers, not only during production, but also fully compensates the amplifiers for long term drift in the ECG amplifier gain from substantially all causes.

Still further according to the invention, the phase-lock-loop circuit in transmitter 20 is self-aligning under microcontroller command upon each power-up to center the voltage controlled oscillator in the phase-lock loop at a nominal center frequency prior to loop activation. This allows not only for full compensation for all long-term component drift, but also the ability to lock onto any frequency or channel in the telemetry band.

Figure 2:
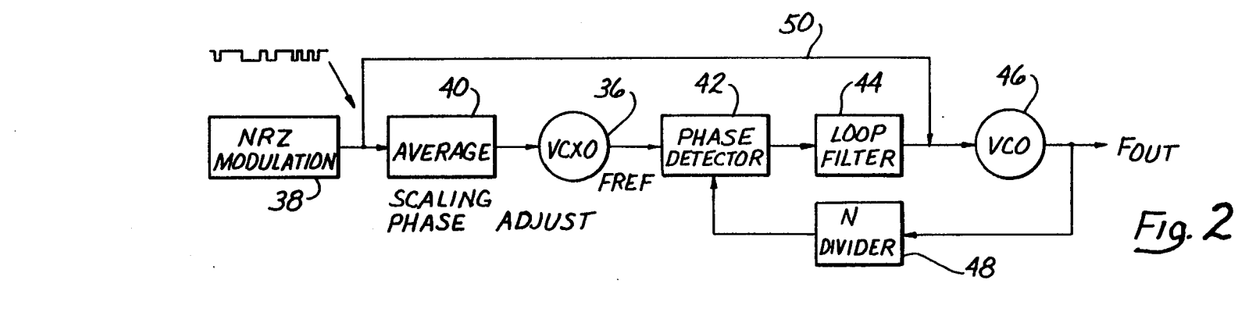
FIG. 2 is a block diagram of a phase-lock-loop circuit used for digital frequency modulation incorporating the invention.

Turn now to FIG. 2 wherein a block diagram of a data bias compensation circuit in a phase-lock loop included in transmitter 20 is depicted. It is a common technique to modulate a phase-lock-loop FM transmitter by using the voltage controlled oscillator (VCO) frequency control input as the modulation port. It is well known that if the phase-lock-loop circuit has a closed loop bandwidth significantly below the modulating frequency, direct frequency modulation of the output of the phase-lock loop's voltage controlled oscillator will result. Digital modulation, such as NRZ modulation, provided to the control input of the VCO may then be used according to the invention for sending biopotential, electrocardiographic or other patient information to receiver 22 in digital format.

However, any signal provided to the input of the VCO will be treated by the phase-lock-loop circuit as an error signal, which the circuit will attempt to reduce to zero, even including the modulation which comprises the desired information. However, because of the limited frequency response of the phase-locked loop, it acts as a high pass circuit, thereby AC coupling the modulating waveform through to the output.

Any modulating signal which has a low frequency or DC components creates a data bias problem, since the low frequency and DC components are well within the phase-lock-loop circuit's bandwidth. Low frequency modulation of the VCO or DC bias will significantly distort the modulated FM waveform which is transmitted. Receiver 22, which observes the VCO signal from transmitter 20, will see the modulation as being AC coupled. For digital modulation this will result in a droop or tilt in the detected output, depending upon the data bit pattern which is being transmitted. Some data bit patterns will be at voltage or frequency levels more nearly corresponding to a logic one while other data bit patterns will be at voltage frequency levels more nearly corresponding to a logic value zero, or at any value in between. If this were not corrected the receiver would need twice the bandwidth it would ordinarily require if low frequency or DC data bias could be eliminated. This in turn deprives the user of half the available channels within the telemetry band.

Figure 3:
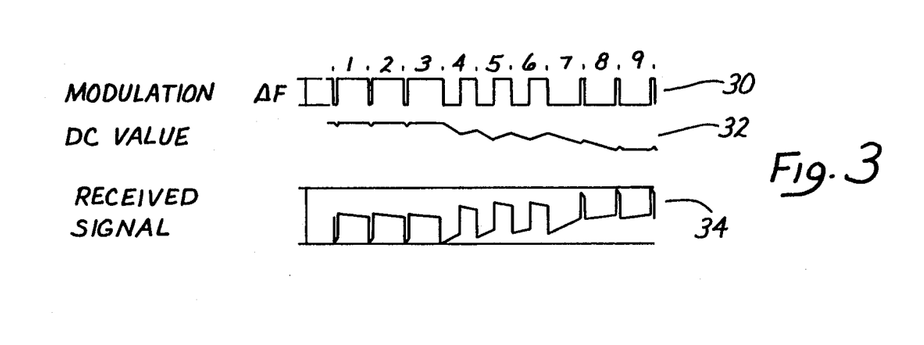
FIG. 3 is a timing diagram showing a sent and received digital signal which is subject to data bias.

FIG. 3 illustrates a typical example of the DC bias from an NRZ bit pattern. Line 30 shows the NRZ bit pattern which is transmitted from A-to-D converter 18. The DC average of the bit pattern of line 30 is depicted by line 32. If there were no DC data bias compensation as provided by the invention, the received data bit pattern seen by receiver 22 would be shown by line 34, which is spread out over nearly twice the bandwidth of the bit pattern of line 30.

Turn now to the block diagram of FIG. 2. Instead of using a fixed reference frequency as the input to the phase-lock-loop circuit, the circuit of FIG. 2 utilizes the output of a voltage controlled crystal oscillator (VCXO) 36 as a variable reference frequency. The input data from instrumentation 14 in FIG. 1 is provided in the illustrated embodiment as serial NRZ data which is diagrammatically depicted in FIG. 2 as output from an NRZ modulation circuit 38. The DC average level of the NRZ bit pattern is generated by averaging circuit 40 which also provides a scaling adjustment. The input to averaging circuit 40 is coupled to the output of NRZ modulation circuit 38. The output of averaging circuit 40 in turn is provided to the control input of VCXO 36. The output reference frequency from VCXO 36 is then provided to the conventional phase detector 42 of the phase-lock-loop circuit. The output of the phase detector in turn is provided through a conventional loop filter 44 and provided to the control input of output VCO 46. The output of VCO 46 is the output frequency of the phase-lock-loop circuit. This output signal is used to generate the transmitter signal from transmitter 20 in a conventional way.

The output of VCO 46 is fed back through an N divider 48 to phase detector 42 in a conventional manner for phase-lock loop control.

However, the NRZ data is also provided from NRZ modulation circuit 38 directly to the control input of VCO 46 to provide high frequency modulation of the output frequency as described above. The NRZ signal drives the control input of the VCO 46. The phase-lock loop highpass filter action allows the high frequency content of the NRZ signal to modulate the VCO 46 with no attenuation, but with resultant droop because of the lack of low frequency response. The low frequency content of the NRZ signal modulates the reference frequency VCXO 36. The phase-lock loop provides a lowpass response to modulation of the reference frequency. The net result of modulating reference VCXO 36 with the low frequency content of the NRZ modulation, and modulating the output VCO 46 with the high frequency content of the NRZ modulation is an overall modulation of the output VCO 46 by the NRZ signal with no tilt or droop due to data bias.

Figure 4:
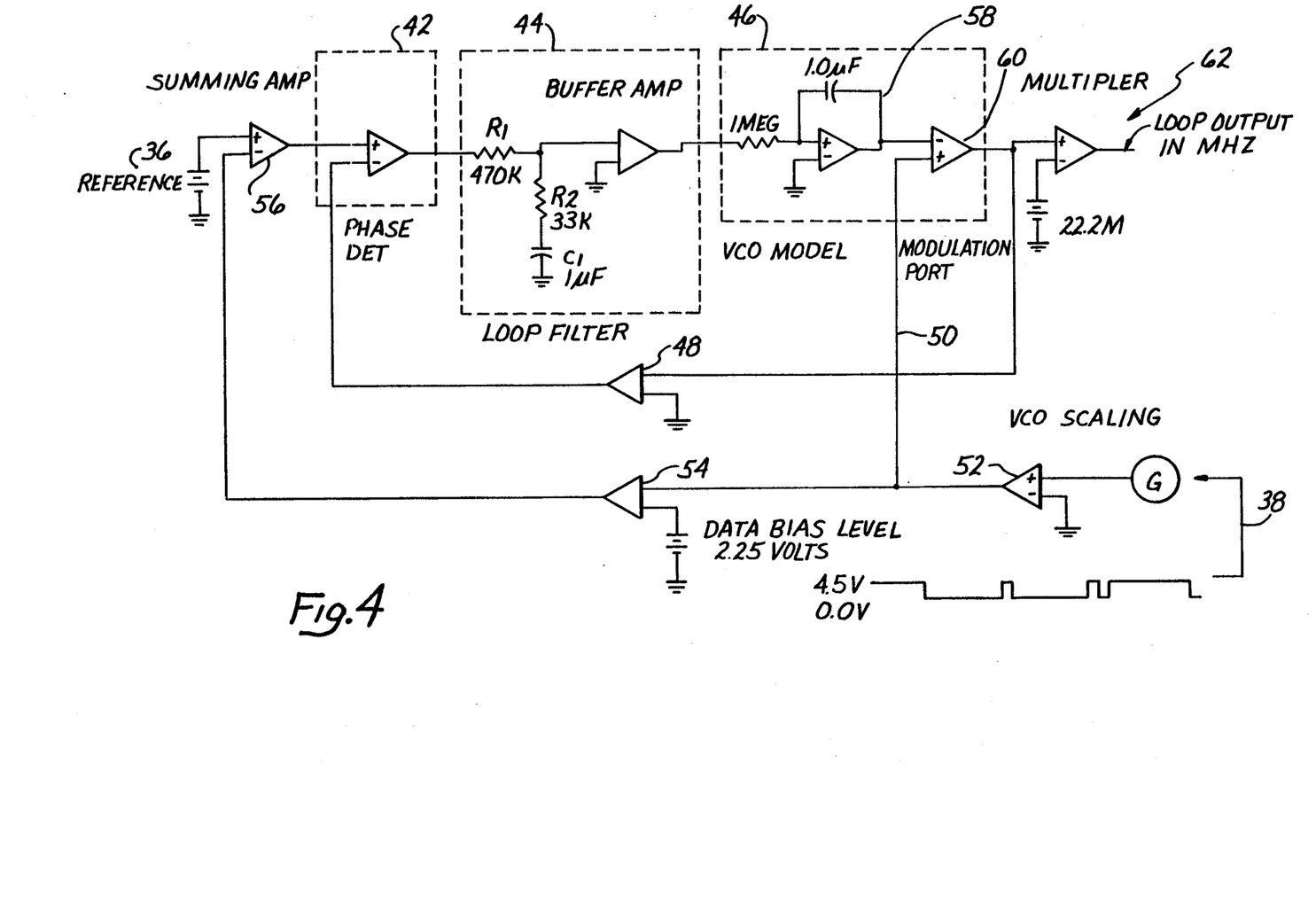
FIG. 4 is a circuit model of a phase-lock-loop circuit illustrating a more detailed depiction of the invention asgenerally illustrated in FIG. 2.

FIG. 4 is a schematic diagram of a circuit model used to analyze the system of FIG. 2 wherein like elements have been reference by like numerals. The NRZ data is input to a VCXO scaling amplifier 52, the output of which is then split to VCO 46 on one hand and to a compensator amplifier 54 on the other. The compensator amplifier adjusts the data bias level to provide a conditioned signal to a summing amplifier 56. The scaled and compensated data bias signal is then added by summing amplifier 56 to a reference signal. The output of summing amplifier 56 is then provided to the input of phase detector 42. Phase detector 42 is coupled to loop filter 44 which in turn is coupled to the input of VCO 46. The output of an oscillator portion 58 within VCO 46 is provided to a differential amplifier 60 wherein it is modulated by the high frequency components of the NRZ data bit pattern provided on line 50. The output of VCO 46 is then multiplied by a multiplier 62 and provided as an RF signal for transmitter 20 for further processing within transmitter 20 as a FSK modulated signal.

Figure 5:
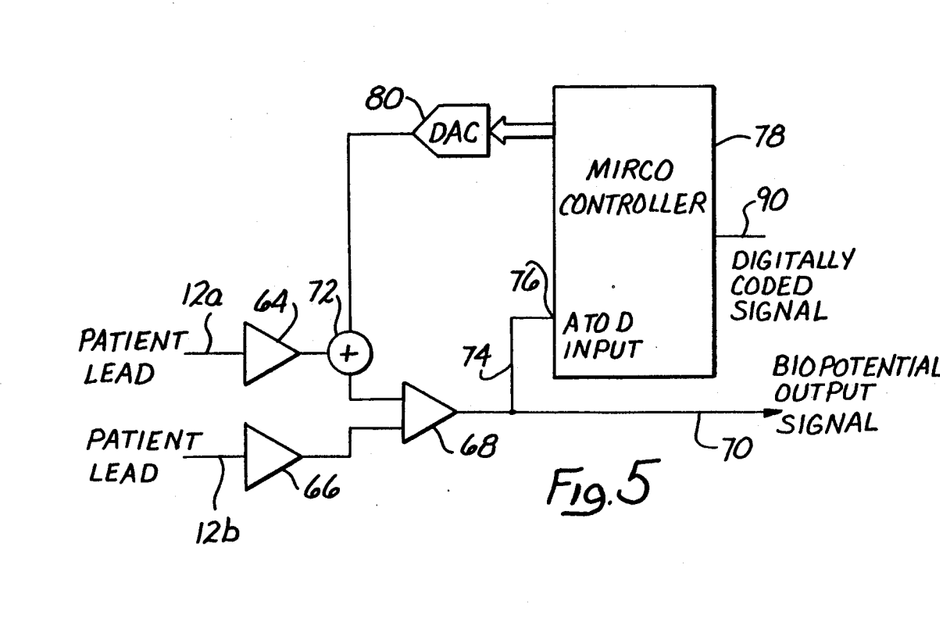
FIG. 5 is a block diagram of an improvement in an instrumentation amplifier, such as an ECG amplifier.

Turn now to the block diagram of FIG. 5 wherein a microcontroller DC tracking loop used to provide DC offset compensation for the ECG amplifiers according to the invention is illustrated. Biopotentials typically have a signal level of 10 millivolts peak to peak, particularly in the case of electrocardiographic signals. Large DC offsets of the order of 300 millivolts are not uncommon. While the prior art has often attempted to avoid DC offsets through AC coupling of the biopotential signals, the corner frequency associated with AC coupling attenuates many clinically important characteristics of the ECG waveshape. AC coupling offers an effective solution to the DC offset problem only in the most primitive noncritical patient monitoring situations. Other prior art attempts of DC coupling the ECG signal include combining the signal with the output of an adjustable voltage divider to keep the waveforms centered in the desired dynamic range. The use of this method is totally impractical in a hospital environment. Still further prior art attempts to use analog circuitry to cancel the effects of the offset voltage. An average value of the offset potential is derived through an analog circuit, such as a low pass filter, and then amplified or signal conditioned and fed back into the input as a bias correction signal. The ECG waveform in such a circuit still appears as though it were AC coupled. To avoid distortion of the ECG signal the time constant of the feedback loop has to be made quite large, typically in the order of several seconds. This large time constant then makes the system incapable of responding quickly to large DC transients.

In addition, the average tracking of the ECG waveform to generate a DC offset fails to take into account the effects of asymmetry of the ECG waveform. If the ECG waveform is highly asymmetric, the average value may be well above or below the voltage midpoint of the ECG amplifier's operating range. When the average is below the midpoint of the operating range, for example, an inappropriate DC bias is generated which may distort or clip off the lower peaks of the waveform. The analog compensation of DC offset centers the DC value of the overall waveform and does not position the center of the peak-to-peak value of the ECG waveform at the ECG amplifier midpoint. As such, it fails to properly compensate for waveform asymmetry.

FIG. 5 is a diagrammatic illustration of the microcontroller offset adjustment of the invention. Patient leads 12a and 12b are provided as an input to buffers 64 and 66. The outputs of buffers 64 and 66 are coupled to a differential amplifier 68 which provides the biopotential output signal on line 70. In the case of the output from buffer 64, the signal from patient lead 12a is coupled through a summing circuit 72. The output signal is also coupled via line 74 to an analog-to-digital converter input 76 in microcontroller 78. Microcontroller 78, which includes memory as well as an analog-to-digital converter, continuously samples the output of the ECG amplifier system. If the DC signal plus peak-to-peak variation of the ECG signal lies within the common mode limit of operation of the amplifier chain as stored within microcontroller 78, no correction is undertaken. There is no AC coupling mechanism within the circuit and the system response will include DC in this mode.

If the signal from patient leads 12a and 12b shift up or down and approaches a predetermined threshold limit, microcontroller 78 programs or sends a word to a digital-to-analog converter 80 to reposition the signal within proper range. At the same time microcontroller 78 modifies the digital information being sent to the receiver to inform the receiver as to the exact amount of the compensation signal. This information is placed as a digitally coded signal on output 90. Receiver 22 uses this information to avoid interpreting compensation feedback as valid ECG data. Since receiver 22 has information concerning prior compensation, processing software in receiver 22 can remove these effects from a displayed waveform and maintain the DC response of the ECG waveform even when the output of digital-to-analog converter 80 is changing.

Figure 6:
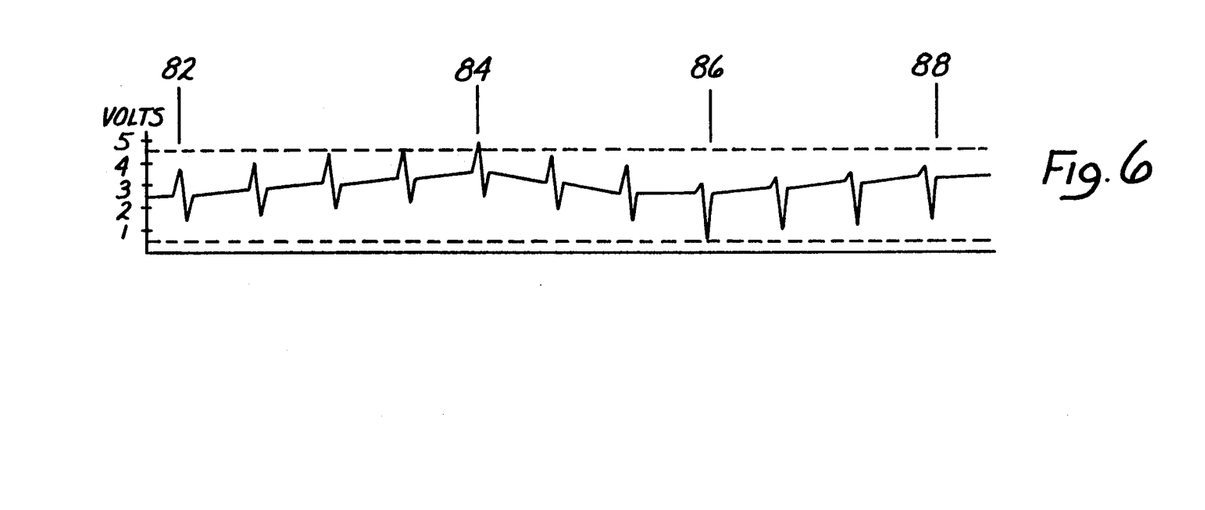
FIG. 6 is a timing diagram of a signal subject to digital compensation of its offset range according to the invention.

Turn now to FIG. 6 wherein an ECG signal subject to DC drift and waveform asymmetry is depicted as seen in the circuitry of FIG. 5. In the depiction of FIG. 6 the dynamic range of the ECG amplifier is between 0.5 and 4.5 volts. At point 82 a symmetrical ECG waveform starts out centered between 0 and 5 volts, namely precisely at 2.5 volts. Since the ECG waveform peak-to-peak limits lies symmetrically between the allowable common mode limits of the ECG amplifier, microcontroller 78 leaves digital-to-analog converter 80 unchanged. Between point 82 and point 84 the waveform exceeds the upper limit of 4.5 volts. Microcontroller 78 tracks this change and when the ECG waveform exceeds the upper common mode limit, microcontroller 78 begins modifying the control word provided to digital-to-analog converter 80 to reposition the ECG waveform between the common mode limits.

At point 86, a different situation arises in which there is no DC offset but the waveform become asymmetrical. A conventional analog control loop can do little to compensate for this type of occurrence. Microcontroller 78, however, recognizes the condition as an asymmetrical waveform and applies a correcting digital input to digital-to-analog converter 80. The response is depicted at point 88 which shows a new high DC level, but one in which the peak-to-peak value of the ECG waveform still remains between the 0.5 and 4.5 volt limits.

Compensation algorithms reside in the software in microcontroller 78 and not in dedicated circuitry. Therefore, compensation schemes which may be applied can be adapted to a wide variety of baseline recovery problems. Most baseline recovery schemes result in the signal experiencing some sort of AC coupling equivalent. Since the microcontroller is capable of placing a signal on the output line 70 indicating what kind of compensation is taking place, the software in the receiving unit 22 can remove any observable effect of the DC compensation no matter what its scheme may be.

Furthermore, microcontroller 78 is programmed according to the invention to calibrate the voltage amplification of each ECG amplifier to its nominal center value on each power-up of the system. Amplifier 68 is a gain programmable amplifier coupled from microcontroller 78. Upon power-up, microcontroller 78 through digital-to-analog converter 80 places a one millivolt test signal into the input of amplifier 68 through summing circuit 72. The output of amplifier 68 is monitored at input 76 of microcontroller 78. Since the input is known and standardized, the output is indicative of the gain of ECG amplifier 68 which is then appropriately corrected through a correction signal generated through software control by microcontroller 78 to gain programmable amplifier 68.

Most phase-lock-loop frequency synthesizer systems use a varactor (varicap) diode to provide a voltage variable frequency characteristic for the voltage controlled oscillator. This causes a tradeoff which is inherent in most phase-lock-loop designs. To reduce the incidental frequency modulation of the phase-lock loop's output, the tuning curve for the voltage controlled oscillator, that is the rate of frequency change per volt of tuning control voltage, should be as small as possible. However, if the range of required output frequencies is large, the varicap diode must have a very large control range. These two requirements are mutually unobtainable in most phase-lock-loop designs. For systems which require the phase-lock-loop circuit to operate over a wide range of frequencies, the alignment of the voltage controlled oscillator can require a significant amount of manual labor and technical skill. This requirement is avoided by utilizing the circuitry shown diagrammatically in FIG. 7a. Two varicap diodes are included within the frequency control circuit of the voltage control oscillator 46 to satisfy the requirements for low phase noise while simultaneously insuring a large tuning range.

Figure 7A:
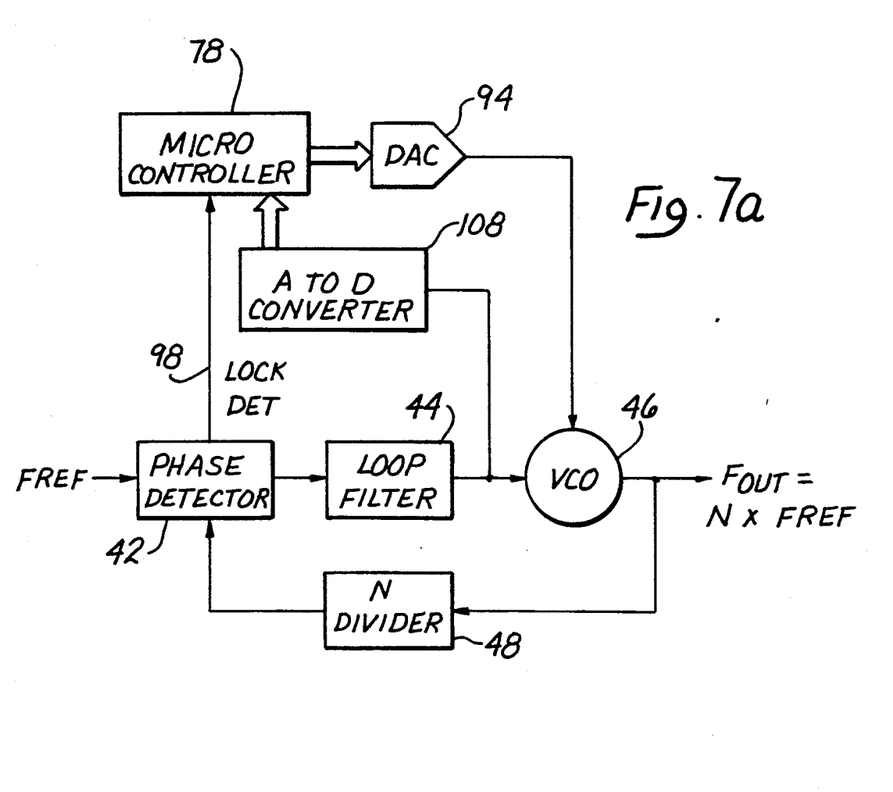
FIG. 7a is a block diagram of an improvement to the tuning of a phase-lock-loop circuit.
Figure 7B:
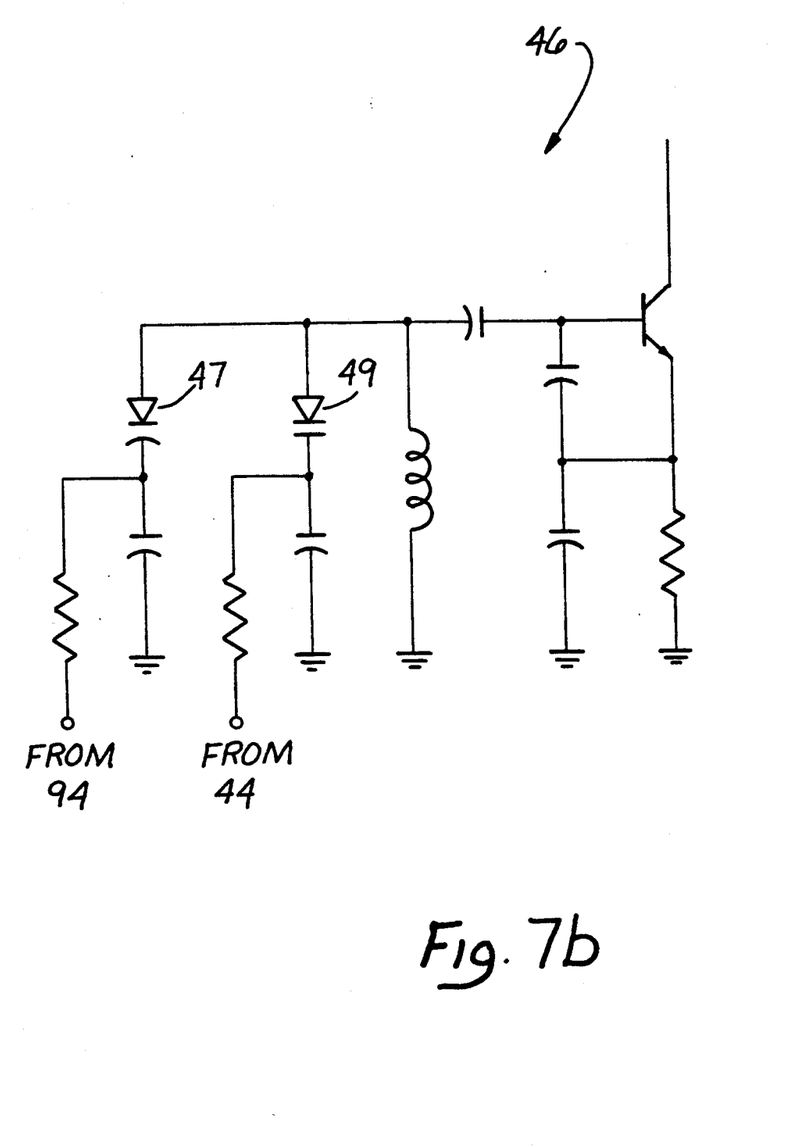
FIG. 7b is a simplified schematic of VCO 46 of FIG. 7a showing the two varicap diodes.

Turn to FIG. 7b wherein a simplified schematic of VCO 46 is depicted. Rather than using a single varicap diode to control the center frequency of VCO 46, one diode 47 is used to provide a coarse tuning capability via the output of a digital-to-analog converter 94 and a microcontroller 78. A second varicap diode 49 is used in VCO 46 which has only sufficient tuning range to satisfy the locking requirement of the phase-lock-loop circuit plus enough excess tuning range to accommodate VCO frequency drift due to temperature, pulling and small external effects.

Microcontroller 78 samples signals, collectively denoted as LOCK DET, on lines 98 from phase detector 42 to determine the lock status of the phase-lock-loop circuit. LOCK DET indicates whether or not the phase-lock-loop circuit has locked and if not, what direction the frequency must change to approach lock. Microcontroller 78 pretunes VCO 46 as close as possible to the desired operating frequency. The microcontroller drives digital-to-analog converter 94, which is an eight-bit circuit, with a successive approximation algorithm to tune the system through eight iterations to within a least significant bit of the desired voltage. The tuning range required by the loop's second varicap diode need only make up for the small amount of VCO error remaining. The eight-bit pretuning allows the prepositioning of the VCO to insure proper lock operation over a large range of output frequencies. Microcontroller 78 fine tunes VCO 46 to place the phase-lock-loop tuning voltage in the design center of its control range. This approach always leaves the phase-lock-loop circuit at the optimum operating point in terms of maximizing the tuning range for the circuit.

Also, since microcontroller 78 monitors the state of the LOCK DET line 98, microcontroller 78 has the ability to reacquire phase-lock operation at any time if the control range of the phase-lock-loop's varicap diode should prove insufficient to maintain phase lock.

Figure 8:
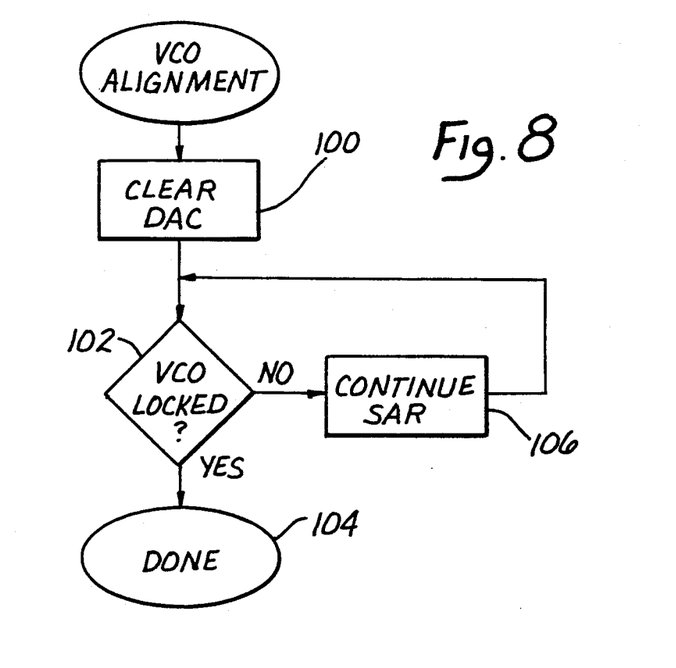

FIG. 8 is a block diagram showing a process whereby microcontroller 78 may operate. At step 100 digital-to-analog converter 94 is cleared to an initial, usually zero, output. At step 102 the microcontroller polls the LOCK DET signals to determine whether or not a phase lock has been achieved. If it has, the process is finished and exits at step 104. However, if phase lock has not been achieved, then a successive approximation routine is implemented at step 106. The successive approximation routine picks a number in the middle of the range of digital-to-analog converter 94 to provide to VCO 46. If digital-to-analog converter 94 was initialized to zero, the midpoint would then next be selected. In almost all instances the midpoint would not result in a phase lock as determined at step 102 and processing would continue to step 106. The LOCK DET signals indicate to microcontroller 78 not only whether phase lock has been achieved, but whether the frequency which is needed is higher or lower than that currently set to the control input lines of VCO 46. If for example a lower signal was required, microcontroller 78 would then set the signal output by digital-to-analog converter 94 to the quarter point of its range. The successive approximation routine would then continue with successive halving steps until eight iterations had been completed and the desired voltage approached to within 1 part in 256. At this point the phase lock look circuit need only concern itself with close-in effects such as phase noise and incidental FM to make the final frequency adjustment with the second varicap diode. Any requirement for critical manual alignment of VCO 46 within its tuning range is thereby avoided. Total immunity to long term component drift and the effects of large temperature shifts are also avoided.

The output from loop filter 44 is provided to analog-to-digital converter 108 and thence to microcontroller 78 which continuously monitor the fine tuning control voltage applied to VCO 46 in order to compensate for any long term component drift or temperature shifts. When component variation causes the control voltage provided to VCO 46 to drift too near a range limit as detected by analog-to-digital converter 108, microcontroller 78 inserts a corrective bias through digital-to-analog converter 94 to reposition VCO 46 at the optimum operating point notwithstanding the component drift.

Another use of the circuitry of FIG. 7a is to preposition VCO 46 within the phase-lock-loop circuit to exploit the nonlinear aspect of the tuning curve of the phase-lock loop's control varicap diode to compensate for loop bandwidth changes resulting from variation in the control of N divider 48. Divider 48 can be changed to generate different output frequencies by changing the value of N and in so doing the loop characteristics of the phase-lock-loop circuit will change in response. In general, increases in N, the value or divide constant of divider 48, decrease the loop bandwidth, while decreases in N increase the loop bandwidth. It turns out from the analysis of the phase loop lock circuit and its characteristic equation that if the oscillator gain of VCO 46 and/or the phase detector gain of phase detector 42 can be made to match the changes in N of frequency divider 48, the loop bandwidth of the phase-lock-loop circuit will remain constant.

Figure 9:
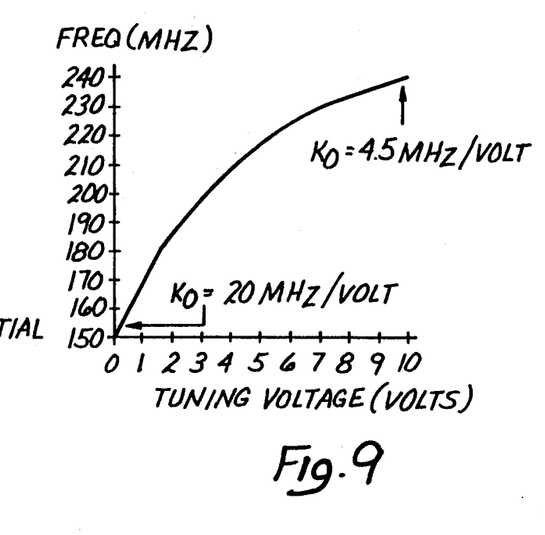

The tuning curve for VCO 46 tuned with the standard varicap diode is nonlinear as graphically depicted in FIG. 9. FIG. 9 shows a typical tuning curve for a varicap diode tuned VCO operating in the 150–240 Mhz tuning range. At the low end of the frequency range, 150 Mhz, the gain of the VCO is 20 MHZ per volt. The oscillator gain at 235 MHZ is, however, 4.5 MHZ per volt. This represents 4.44/1 variation in oscillator gain from one end of the band to the other. By prepositioning VCO 46 at a point on the tuning curve where the oscillator gain compensates for changes in the quantity N of divider 48, the loop bandwidth of the phase-lock-loop circuit could be held constant over the entire tuning range. This is accomplished as follows.

As described in connection with the flow diagram of FIG. 8, microcontroller 78 positions digital-to-analog converter 94 to within one least significant bit of the exact VCO frequency required for phase lock. Now, rather than fine tuning digital-to-analog converter 94 to place the phase-lock loop's control voltage within the center of its tuning range, microcontroller 78 fine tunes the output of digital-to-analog controller 94 to place the phase lock loop control voltage at a point on the VCO tuning curve of FIG. 9 which compensates for the user selected value of N of divider circuit 48. To achieve this purpose, the values of the tuning curve of FIG. 9 are stored within a memory within microcontroller 78.

Therefore, the microcontroller can be used to self-align the phase-lock-loop circuit at a point in the tuning curve which always compensates for changes in the frequency of divider 48 while a second varicap diode provides the fine tuning of the phase-lock-loop circuit.

Either one of the above described tuning procedures, used alone or together, provides significant improvement in the operation of the phase-lock-loop circuit over a wide frequency range. The requirement for a large amount of alignment and calibration time is avoided and the loop maintains its nominal design center even in the presence of component drift, aging and temperature shifts.

Many modifications and alterations may be made by those having ordinary skill in the art without departing from the spirit and scope of the invention. Therefore, the illustrated embodiment has been set forth only for the purposes of example and should not be taken as limiting the invention as defined in the following claims. The following claims are thus to be read to include not only the elements literally included, but all equivalents thereto and means for performing substantially the same function to obtain substantially the same result even in a substantially different way.

We claim:

1. An improvement in a biomedical apparatus for monitoring biopotentials derived from a patient comprising:
   instrumentation means for detecting said biopotentials from said patient and for processing an analog signal at said patient corresponding thereto;
   analog-to-digital conversion means for converting said analog signals corresponding to said biopotential signals to digital format at the situs of said patient; and
   transmitter means for telemetering digital signals corresponding to said digitized biopotential signals generated by said analog-to-digital conversion means, said transmitter means being a tunable frequency modulated radio transmitter,
   wherein said digital signals have a pattern characterized by a DC data bias and wherein said tunable frequency modulated radio transmitter comprises:
   an averaging means for averaging said pattern of said digital signals to generate a DC value signal of said pattern;
   first voltage controlled crystal oscillator means having its control input coupled to said averaging means, said first voltage controlled crystal oscillator means for generating a variable reference frequency dependent upon said DC value signal of said pattern of said digital signals;
   a phase detector having its input coupled to an output of said first voltage controlled crystal oscillator means;
   a loop filter having an input coupled to an output of said phase detector;
   a second voltage controlled oscillator means having a control input coupled to an output of said loop filter, an output of said second voltage control oscillator generating an output frequency of said phase-lock-loop circuit within said tunable frequency modulated radio transmitter;
   divider means for feeding back said output frequency to said phase detector divided by a predetermined integer; and
   wherein said digital signals is also coupled into said input of said second voltage controlled oscillator means so that said output frequency of said second voltage controlled oscillator means is frequency modulated by said digital signals and so that said DC data bias is compensated by said DC value signal corresponding to an average DC value of said pattern of said digital data,
   whereby biomedical information is directly telemetered from a patient in digital format.

2. The improvement of claim 1 further comprising:
   receiver means for receiving said telemetered digital signal; and
   computer means coupled to said receiver means for processing said digital signals received by said receiver means at a central station remote from said patient.

3. An improvement in a biomedical apparatus for monitoring biopotentials derived from a patient comprising:
   instrumentation means for detecting said biopotentials from said patient and for processing an analog signal at said patient corresponding thereto;
   analog-to-digital conversion means for converting said analog signals corresponding to said biopotential signals to digital format at the situs of said patient; and
   transmitter means for telemetering digital signals corresponding to said digitized biopotential signals generated by said analog-to-digital conversion means, said transmitter means being a tunable frequency modulated radio transmitter,
   wherein said tunable frequency modulated radio transmitter includes a phase-lock-loop circuit comprising:
   a phase detector having an input for receiving an input frequency, and an output;
   a loop filter having an input coupled to the output of said phase detector, and an output;
   a voltage controlled oscillator for generating an output frequency in response to a control input coupled to an output from said loop filter;
   a divider for feeding back said output frequency to said phase detector divided by a selected integer;
   a microcontroller coupled to a lock detect signal from said phase detector, said lock detect signal signifying whether or not said phase-lock-loop circuit has achieved lockup and if not, whether the desired frequency is greater or less than that at which said voltage controlled oscillator is positioned;
   a digital-to-analog converter coupled to said microcontroller and controlled thereby, said digital-to-analog controller having an output coupled in turn to said voltage controlled oscillator to preposition said voltage controlled oscillator at a frequency as determined by input to said digital-to-analog converter from said microcontroller.

4. The improvement of claim 3 wherein said voltage controlled oscillator comprises:
   a first varicap diode means controlled by said output of said loop filter for fine tuning said voltage controlled oscillator; and
   a second varicap diode means controlled by said output from said digital-to-analog converter for prepositioning said voltage controlled oscillator at a predetermined frequency within a selected band.

5. The improvement of claim 4 further comprising:
   an analog-to-digital converter having an input coupled to said output of said loop filter and an output coupled to said microcontroller, said microcontroller monitoring said output of said analog-to-digital converter for generating an error compensation signal coupled to said digital-to-analog converter in order to maintain said voltage controlled oscillator at a predetermined operating point notwithstanding component drift and large temperature shifts.

6. The improvement of claim 3 wherein said digital signals have a pattern characterized by a DC data bias and wherein said tunable frequency modulated radio transmitter further comprises:
   an averaging means for averaging said pattern of said digital signals to generate a DC value signal;
   a compensating voltage controlled crystal oscillator means having its control input coupled to said averaging means, said compensating voltage controlled crystal oscillator means for generating a variable reference frequency dependent upon said DC value signal of said pattern of said digital signals;
   wherein said phase detector has its input coupled to said output of said compensating voltage controlled crystal oscillator means; and
   wherein said digital data is also coupled into said input of said voltage controlled crystal oscillator so that said output frequency of said controlled crystal oscillator is frequency modulated by said digital data, and so that DC data bias is compensated by said DC value signal corresponding to an average DC value of said pattern of said digital data.

7. The improvement of claim 3 wherein said voltage controlled crystal oscillator has a tuning curve relating frequency of operation and tuning voltage input in said voltage controlled crystal oscillator, and wherein said tuning curve is nonlinear, said microcontroller further comprising means for storing said tuning curve, said microcontroller providing a control signal to said digital-to-analog converter for prepositioning said frequency within said voltage controlled crystal oscillator so that said bandwidth of said phase-lock-loop circuit is substantially constant even though said selected integer dividing said feedback frequency through said divider varies.

8. The improvement of claim 7 wherein said voltage controlled oscillator comprises:
   a first varicap diode means controlled by said output of said loop filter for fine tuning said voltage controlled oscillator; and
   a second varicap diode means controlled by said output from said digital-to-analog converter for prepositioning said voltage controlled oscillator at a predetermined frequency within a selected bandwidth.

9. An improvement in a biomedical apparatus for monitoring biopotentials derived from a patient comprising:
   instrumentation means for detecting said biopotentials from said patient and for processing an analog signal at said patient corresponding thereto;
   analog-to-digital conversion means for converting said analog signals corresponding to said biopotential signals to digital format at the situs of said patient; and
   transmitter means for telemetering digital signals corresponding to said digitized biopotential signals generated by said analog-to-digital conversion means,
   wherein said instrumentation means comprises:
   a biopotential amplifier, said biopotential amplifier receiving said biopotential signals from said patient and for generating an output signal, and having an input,
   said improvement further comprising:
   a microcontroller having an input coupled to said output signal; and
   a digital-to-analog converter having an input coupled to said microcontroller, an output of said digital-to-analog converter being fed back to said amplifier as a correction signal, said microcontroller for determining a DC value of said output signal and for generating a correction signal coupled to said input of said digital-to-analog converter so that said DC value is removed from said output signal by signal compensation into said input of said amplifier.

10. The improvement of claim 9 wherein said amplifier is a digitally programmable gain amplifier with adjustable gain controlled by said microcontroller, said microcontroller being programmed to selectively provide a standardized test signal fed back through said digital-to-analog converter to said amplifier, said microcontroller measuring said output signal from said amplifier and generating a control signal to adjust said gain of said amplifier so that said gain is calibrated to a predetermined value.

11. The improvement of claim 10 wherein said amplifier is an electrocardiographic amplifier for receiving electrocardiographic signals from said patient and for producing an electrocardiographic output signal.

* * * * *